United States Patent
Wu et al.

(10) Patent No.: US 8,691,073 B2
(45) Date of Patent: Apr. 8, 2014

(54) ENZYMATIC ELECTROCHEMICAL BIOSENSOR

(75) Inventors: Huan-Ping Wu, Granger, IN (US); Greg P. Beer, Cassopolis, MI (US); Christina Blaschke, White Pigeon, MI (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 13/214,643

(22) Filed: Aug. 22, 2011

(65) Prior Publication Data

US 2012/0037514 A1  Feb. 16, 2012

Related U.S. Application Data

(63) Continuation of application No. 10/576,485, filed on Apr. 21, 2006, now Pat. No. 8,007,656, which is a continuation of application No. PCT/US2004/035286, filed on Oct. 22, 2004.

(60) Provisional application No. 60/513,817, filed on Oct. 24, 2003.

(51) Int. Cl.
*G01N 27/416* (2006.01)
*G01N 27/327* (2006.01)

(52) U.S. Cl.
USPC ............ 205/777.5; 204/403.02; 204/403.04; 205/792

(58) Field of Classification Search
USPC .............. 204/403.01–403.15, 412; 205/775, 205/777.5, 792, 789
See application file for complete search history.

(56) References Cited

U.S. PATENT DOCUMENTS

| | | |
|---|---|---|
| 3,791,933 A | 2/1974 | Wenz et al. |
| 3,791,988 A | 2/1974 | Dieter et al. |
| 4,746,607 A | 5/1988 | Mura et al. |
| 5,108,564 A | 4/1992 | Szuminsky et al. |
| 5,120,420 A | 6/1992 | Nankai et al. |
| 5,128,015 A | 7/1992 | Szuminsky et al. |
| 5,206,147 A | 4/1993 | Hoenes |
| 5,262,035 A | 11/1993 | Gregg et al. |
| 5,264,104 A | 11/1993 | Gregg et al. |

(Continued)

FOREIGN PATENT DOCUMENTS

| | | |
|---|---|---|
| EP | 0330517 | 2/1989 |
| EP | 0354441 | 2/1990 |

(Continued)

OTHER PUBLICATIONS

International Searching Authority, "International Search Report and Written Opinion for PCT/US2004/035286", Jan. 21, 2005, Publisher: European Patent Office, Published in: EP.

(Continued)

*Primary Examiner* — Keith Hendricks
*Assistant Examiner* — Kourtney S Carlson
(74) *Attorney, Agent, or Firm* — Blanchard & Associates

(57) ABSTRACT

An electrochemical sensor strip has a base and a first electrode and a second electrode on the base. An oxidoreductase enzyme and a mediator are on the first electrode, and a soluble redox species is on the second electrode. The soluble redox species may be an organotransition metal complex, a transition metal coordination complex, an electroactive organic molecule, or mixtures thereof.

14 Claims, 11 Drawing Sheets

(56) References Cited

U.S. PATENT DOCUMENTS

| | | | |
|---|---|---|---|
| 5,288,387 | A | 2/1994 | Ito et al. |
| 5,288,636 | A | 2/1994 | Pollmann et al. |
| 5,320,725 | A | 6/1994 | Gregg et al. |
| 5,356,786 | A | 10/1994 | Heller et al. |
| 5,385,846 | A | 1/1995 | Kuhn et al. |
| 5,520,786 | A * | 5/1996 | Bloczynski et al. ..... 204/403.14 |
| 5,545,519 | A | 8/1996 | Vadgama et al. |
| 5,582,697 | A | 12/1996 | Ikeda et al. |
| 5,620,579 | A | 4/1997 | Genshaw et al. |
| 5,628,890 | A | 5/1997 | Carter et al. |
| 5,653,863 | A * | 8/1997 | Genshaw et al. .......... 205/777.5 |
| 5,660,791 | A | 8/1997 | Brenneman et al. |
| 5,682,884 | A | 11/1997 | Hill et al. |
| 5,695,947 | A | 12/1997 | Guo et al. |
| 5,755,953 | A | 5/1998 | Henning et al. |
| 5,759,364 | A | 6/1998 | Charlton et al. |
| 5,762,770 | A | 6/1998 | Pritchard et al. |
| 5,798,031 | A | 8/1998 | Charlton et al. |
| 5,820,551 | A | 10/1998 | Hill et al. |
| RE36,268 | E | 8/1999 | Szuminsky et al. |
| 6,153,069 | A | 11/2000 | Pottgen et al. |
| 6,258,229 | B1 | 7/2001 | Winarta et al. |
| 6,284,125 | B1 | 9/2001 | Hodges et al. |
| 6,287,451 | B1 | 9/2001 | Winarta et al. |
| 6,297,697 | B2 | 10/2001 | Delano et al. |
| 6,413,411 | B1 | 7/2002 | Pottgen et al. |
| 6,484,046 | B1 | 11/2002 | Say et al. |
| 6,531,040 | B2 | 3/2003 | Musho et al. |
| 6,599,407 | B2 | 7/2003 | Taniike et al. |
| 6,767,441 | B1 | 7/2004 | Cai et al. |
| 6,841,052 | B2 | 1/2005 | Musho et al. |
| 7,431,820 | B2 * | 10/2008 | Hodges ...................... 205/777.5 |
| 2001/0006149 | A1 | 7/2001 | Taniike et al. |
| 2001/0052470 | A1 | 12/2001 | Hodges et al. |
| 2002/0185375 | A1 | 12/2002 | Wogoman |
| 2004/0007461 | A1 | 1/2004 | Edelbrock |
| 2004/0253367 | A1 | 12/2004 | Wogoman |
| 2009/0045076 | A1 * | 2/2009 | Burke et al. .................. 205/792 |

FOREIGN PATENT DOCUMENTS

| | | |
|---|---|---|
| EP | 0909952 | 4/1999 |
| EP | 1691192 | 3/2004 |
| EP | 1707953 | 4/2006 |
| EP | 1742045 | 1/2007 |
| WO | 2005040407 | 5/2005 |

OTHER PUBLICATIONS

Cassidy, et al., "Novel Electrochemical Device for the Detection of Cholesterol Glucose", "Analyst", 1993, pp. 415-418, vol. 118.

Chaubey, et al., "Mediated biosensors", "Biosensors & Bioelectronics", 2002, pp. 441-456, No. 17.

Fultz, et al., "Mediator Compounds for the Electrochemical Study of Biological Redox System: A Compilation", "Analytica Chimica Acta.", 1982, pp. 1-18, vol. 140.

Ho et. al., "Electrochemical Sensor for Measurements of Urea and Creatinine in Serum Based on ac impedance Measurment of Enzyme-Catal", "Anal. Chem", 1999, pp. 1940-1946, vol. 71.

Morris et al., "An Electrochemical Capillary Fill Device for the Analysis of Glucose Incorporating Glucose Oxidase and Ruthenium (III) H", "Electroanalysis", 1992, pp. 1-9, vol. 4, Publisher: VCH Publishers, Inc.

Razumiene et. al., "Improvement of screen-printed carbon electrodes by modifications with ferreocene derivative", "Sensors and Actuators B, Elesvier Sequioa", 2003, pp. 378-383, vol. 95, No. 1-3.

A.D. Smith, Ed., "Oxford Dictionary of Biochemistry and Molecular Biology, Revised Edition", 2000, pp. 161,476,477,560, Publisher: Oxford University Press.

Vidal JC, et al., "A Chronoamperometric sensor for hydrogen peroxide based on electron transfer between immobilized horseradish peroxide ba", "Sensors and Actuators", 1994, pp. 135-141, vol. 21, No. 2, Publisher: Elsevier Science S.A., Published in: Analytical Chemistry Department, Faculty of Sciences, University of Zaragoza. 50009 Zaragoza, Spain.

Wilson, et al., "Glucose oxidase: an ideal enzyme", "Biosensors & Bioelectronics", 1992, pp. 165-185, vol. 7.

* cited by examiner

ENZYMATIC ELECTROCHEMICAL BIOSENSOR

REFERENCE TO RELATED APPLICATIONS

This application is a continuation of U.S. Nonprovisional application Ser. No. 10/576,485, filed Apr. 21, 2006, entitled "Enzymatic Electrochemical Biosensor", which was the National Stage of International Application No. PCT/US04/35286, filed Oct. 22, 2004, entitled "Enzymatic Electrochemical Biosensor", which was published in English and claims the benefit of U.S. Provisional Application No. 60/513,817, filed Oct. 24, 2003, entitled "Enzymatic Electrochemical Biosensor".

BACKGROUND

In monitoring medical conditions and the response of patients to efforts to treat medical conditions, it is desirable to use analytical methods that are fast, accurate, and convenient for the patient. Electrochemical methods have been useful for quantifying certain analytes in body fluids, particularly in blood samples. Typically, these analytes undergo oxidation-reduction reactions when in contact with specific enzymes, and the electric current generated by these reactions can be correlated with the concentration of the analyte of interest. Miniaturized versions of analytical electrochemical cells have been developed that allow patients to monitor levels of particular analytes on their own, without the need for a healthcare provider or clinical technician. Typical patient-operated electrochemical sensors utilize a single measuring unit containing the necessary circuitry and output systems. In use, this unit is connected to a disposable analysis strip containing the electrodes and the necessary reagents to measure the electrochemical properties of a sample that is applied to the strip. The most common of these miniature electrochemical systems are the glucose sensors that provide measurements of blood glucose levels. Ideally, a miniature sensor for glucose should provide accurate readings of blood glucose levels by analyzing a single drop of blood, typically from 1-15 microliters ($\mu$L).

In a typical analytical electrochemical cell, regardless of the size of the system, the oxidation or reduction half-cell reaction involving the analyte either produces or consumes electrons. This electron flow can be measured, provided the electrons can interact with a working electrode that is in contact with the sample to be analyzed. The electrical circuit is completed through a counter electrode that is also in contact with the sample. A chemical reaction also occurs at the counter electrode, and this reaction is of the opposite type (oxidation or reduction) relative to the type of reaction at the working electrode. See, for example, *Fundamentals Of Analytical Chemistry*, 4$^{th}$ Edition, D. A. Skoog and D. M. West; Philadelphia: Saunders College Publishing (1982), pp 304-341.

In some conventional miniature electrochemical systems used for diagnostics, a combination counter/reference electrode is employed. This type of combination electrode is possible when the reference electrode materials are separated, by their insolubility, from the reaction components of the analysis solution. Counter/reference electrodes are typically a mixture of silver (Ag) and silver chloride (AgCl), which exhibits stable electrochemical properties due to the insolubility of its components in the aqueous environment of the analysis solution. Since the ratio of Ag to AgCl is not significantly changed during use, the electrochemical properties of the electrode are likewise not significantly changed.

Although the Ag/AgCl electrode functions well as a reference electrode, it can be less than ideal in its function as a counter electrode. The Ag/AgCl material has a high resistivity, which inhibits its capacity for carrying electrical current. Thus, high voltages and/or current levels may be necessary to operate the sensor. This can be especially problematic in miniaturized electrochemical analysis strips, since small uncertainties and variabilities can dramatically reduce the sensitivity of the measurement. Samples containing high concentrations of the analyte can yield erroneous results if the high current produced through reaction of the analyte is impeded by the counter electrode.

Another feature of some conventional miniaturized electrochemical strips is the presence of a single layer of reagents over both the working and counter electrodes. The components of this reagent layer include the enzyme that facilitates the oxidation-reduction reaction of the analyte, as well as any mediators or other substances that help to transfer electrons between the oxidation-reduction reaction and the working electrode. The use of a single reagent layer can provide for simple manufacturing of the strips, since only one deposition step coats the material onto the electrodes. A disadvantage of the single layer construction is that each electrode is in contact with the same environment when the device is in use. Thus, the individual environment of each electrode is not controlled to provide the optimum conditions for electrode function. This lack of optimization can also reduce the sensitivity of the system.

There is a need for miniaturized electrochemical systems with improved sensitivity to the concentration of analytes in patient samples. It is desirable for miniaturized electrochemical strips to contain independently optimized electrodes having high conductivities.

SUMMARY

In one aspect of the invention, there is an electrochemical sensor strip, comprising a base; a first electrode on the base; a second electrode on the base; an oxidoreductase enzyme and a mediator on the first electrode; and a soluble redox species on the second electrode.

In another aspect of the invention, there is an electrochemical sensor strip, comprising a base; a first electrode on the base; a second electrode on the base; an enzyme on the first electrode, where the enzyme is glucose oxidase, glucose dehydrogenase or a mixture thereof; a mediator on the first electrode; and a soluble redox species on the second electrode. The soluble redox species is preferably an organotransition metal complex, a transition metal coordination complex or mixtures thereof.

In yet another aspect of the invention, there is a method of making an electrochemical sensor strip, comprising depositing a first electrode on a base; depositing a second electrode on the base; applying a first layer onto the first electrode, the first layer comprising an oxidoreductase and a mediator; and applying a second layer onto the second electrode, the second layer comprising a soluble redox species.

In yet another aspect of the invention, there is a method of quantifying an analyte in a sample, comprising contacting the sample with an electrochemical sensor strip; the electrochemical sensor strip comprising a first electrode and a first layer on the first electrode, the first layer comprising an oxidoreductase enzyme and a mediator; the electrochemical sensor strip also comprising a second electrode and a second layer on the second electrode, the second layer comprising a soluble redox species; applying an electrical potential between the first and second electrodes; measuring a current passing through the first and second electrodes and the sample; and correlating the current to a concentration of the analyte.

DETAILED DESCRIPTION

Figure 1:
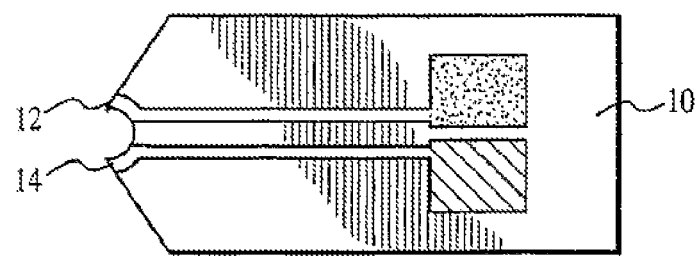
FIG. 1 is a top view diagram of a sensor base containing a working electrode and a counter electrode.

The present invention relates to an electrochemical biosensor for determining the presence or amount of a substance in a sample. The biosensor includes sensor strips containing a working electrode and a counter electrode, each of which is at least partially covered with a separate reagent layer. The reagent layer on the working electrode includes an enzyme that interacts with an analyte through an oxidation-reduction reaction and also includes a mediator. The reagent layer on the counter electrode includes a soluble redox species that can undergo the opposite type of oxidation-reduction reaction with respect to the analyte reaction. The soluble redox species is preferably present in the counter electrode reagent layer in a molar amount greater than that of its counterpart species, where the redox species and its counterpart species together are a redox pair. Sensors of the present invention may provide for improvements in accuracy, range of analysis, and shelf life.

The term "sample" is defined as a composition containing an unknown amount of the analyte of interest. Typically, a sample for electrochemical analysis is in liquid form, and preferably the sample is an aqueous mixture. A sample may be a biological sample, such as blood, urine or saliva. A sample may be a derivative of a biological sample, such as an extract, a dilution, a filtrate, or a reconstituted precipitate.

The term "analyte" is defined as a substance in a sample, the presence or amount of which is to be determined. An analyte interacts with the oxidoreductase enzyme present during the analysis, and can be a substrate for the oxidoreductase, a coenzyme, or another substance that affects the interaction between the oxidoreductase and its substrate.

The term "oxidoreductase" is defined as any enzyme that facilitates the oxidation or reduction of a substrate. The term oxidoreductase includes "oxidases," which facilitate oxidation reactions in which molecular oxygen is the electron acceptor; "reductases," which facilitate reduction reactions in which the analyte is reduced and molecular oxygen is not the analyte; and "dehydrogenases," which facilitate oxidation reactions in which molecular oxygen is not the electron acceptor. See, for example, *Oxford Dictionary of Biochemistry and Molecular Biology, Revised Edition*, A. D. Smith, Ed., New York: Oxford University Press (1997) pp. 161, 476, 477, and 560.

The term "oxidation-reduction" reaction is defined as a chemical reaction between two species involving the transfer of at least one electron from one species to the other species. This type of reaction is also referred to as a "redox reaction." The oxidation portion of the reaction involves the loss of at least one electron by one of the species, and the reduction portion involves the addition of at least one electron to the other species. The ionic charge of a species that is oxidized is made more positive by an amount equal to the number of electrons transferred. Likewise, the ionic charge of a species that is reduced is made less positive by an amount equal to the number of electrons transferred.

The term "oxidation number" is defined as the formal ionic charge of a chemical species, such as an atom. A higher oxidation number, such as (III), is more positive, and a lower oxidation number, such as (II), is less positive. A neutral species has an ionic charge of zero. Oxidation of a species results in an increase in the oxidation number of that species, and reduction of a species results in a decrease in the oxidation number of that species.

The term "redox pair" is defined as two species of a chemical substance having different oxidation numbers. Reduction of the species having the higher oxidation number produces the species having the lower oxidation number. Alternatively, oxidation of the species having the lower oxidation number produces the species having the higher oxidation number.

The term "oxidizable species" is defined as the species of a redox pair having the lower oxidation number, and which is thus capable of being oxidized into the species having the higher oxidation number. Likewise, the term "reducible species" is defined as the species of a redox pair having the higher oxidation number, and which is thus capable of being reduced into the species having the lower oxidation number.

The term "soluble redox species" is defined as a substance that is capable of undergoing oxidation or reduction and that is soluble in water (pH 7, 25° C.) at a level of at least 1.0 grams per Liter. Soluble redox species include electroactive organic molecules, organotransition metal complexes, and transition metal coordination complexes. The term "soluble redox species" excludes elemental metals and lone metal ions, especially those that are insoluble or sparingly soluble in water.

The term "organotransition metal complex," also referred to as "OTM complex," is defined as a complex where a transition metal is bonded to at least one carbon atom through a sigma bond (formal charge of −1 on the carbon atom sigma bonded to the transition metal) or a pi bond (formal charge of 0 on the carbon atoms pi bonded to the transition metal). For example, ferrocene is an OTM complex with two cyclopentadienyl (Cp) rings, each bonded through its five carbon atoms to an iron center by two pi bonds and one sigma bond. Another example of an OTM complex is ferricyanide (III) and its reduced ferrocyanide (II) counterpart, where six cyano ligands (formal charge of −1 on each of the 6 ligands) are sigma bonded to an iron center through the carbon atoms of the cyano groups.

The term "coordination complex" is defined as a complex having well-defined coordination geometry, such as octahedral or square planar geometry. Unlike OTM complexes, which are defined by their bonding, coordination complexes are defined by their geometry. Thus, coordination complexes may be OTM complexes (such as the previously mentioned ferricyanide), or complexes where non-metal atoms other than carbon, such as heteroatoms including nitrogen, sulfur, oxygen, and phosphorous, are datively bonded to the transition metal center. For example, ruthenium hexaamine is a coordination complex having a well-defined octahedral geometry where six $NH_3$ ligands (formal charge of 0 on each of the 6 ligands) are datively bonded to the ruthenium center. A more complete discussion of organotransition metal complexes, coordination complexes, and transition metal bonding may be found in Collman et al., *Principles and Applications of Organotransition Metal Chemistry* (1987) and Miessler & Tarr, *Inorganic Chemistry* (1991).

The term "mediator" is defined as a substance that can be oxidized or reduced and that can transfer one or more electrons between a first substance and a second substance. A mediator is a reagent in an electrochemical analysis and is not the analyte of interest. In a simplistic system, the mediator undergoes a redox reaction with the oxidoreductase after the oxidoreductase has been reduced or oxidized through its contact with an appropriate substrate. This oxidized or reduced mediator then undergoes the opposite reaction at the electrode and is regenerated to its original oxidation number.

The term "electroactive organic molecule" is defined as an organic molecule that does not contain a metal and that is capable of undergoing an oxidation or reduction reaction. Electroactive organic molecules can behave as redox species and as mediators. Examples of electroactive organic molecules include coenzyme pyrroloquinoline quinone (PQQ), benzoquinones and naphthoquinones, N-oxides, nitroso compounds, hydroxylamines, oxines, flavins, phenazines, phenothiazines, indophenols, and indamines.

The term "electrode" is defined as an electrically conductive substance that remains stationary during an electrochemical analysis. Examples of electrode materials include solid metals, metal pastes, conductive carbon, conductive carbon pastes, and conductive polymers.

The term "non-ionizing material" is defined as a material that does not ionize during the electrochemical analysis of an analyte. Examples of non-ionizing materials include carbon, gold, platinum and palladium.

The term "on" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating can be described as "on" the first element. Thus, the use of the term "on" may or may not mean that the two elements being related are in physical contact with each other.

Electrochemical analytical sensors can be constructed in a variety of ways and using a variety of materials. See, for example, U.S. Pat. Nos. 5,120,420 and 5,798,031, both of which are incorporated herein by reference. Referring to FIGS. 1-3 and 12-15, in general, electrode materials are deposited onto a base material 10. The base material is preferably an electrical insulator so as to isolate the electrochemical system from its surroundings. The electrode materials can be configured to connect to outside circuitry, for example through conductors 12 and 14. These connections allow the electrochemical response of the sensor to be monitored and/or manipulated. Preferably, the electrode materials and the entire sensor are configured to be compatible with existing electroanalytical measurement devices. In addition, the electrode materials are configured to provide contact with the sample to be analyzed. Each electrode is coated with a layer of material containing appropriate analytical reagents. The working electrode 20 is coated with a first layer 26 containing an oxidoreductase enzyme and a mediator. The counter electrode 30 is coated with a second layer 36 containing a soluble redox species. The electrodes may be partially covered by a dielectric layer 40, such as an insulating polymer, to isolate the portions of the electrodes that are in contact with the reagent layers from the portions that connect the electrodes to outside circuitry. This dielectric layer, if present, may be deposited before, during or after the coating of the electrodes with the appropriate reagent layer. The entire assembly is then covered at least partially with a lid 50. Preferably the lid covers, but does not contact, the reagent layers, so as to providing a space for the sample to be deposited and analyzed. Optional third electrode 70 is coated with a third layer 76 containing a soluble redox species. The optional third electrode may be configured to connect to outside circuitry through conductor 13.

Each electrode may contain any electrically conductive substance, including metals, conductive polymers, and conductive carbon. Examples of conductive materials include a thin layer of a metal such as gold, silver, platinum, palladium, copper, or tungsten, as well as a thin layer of conductive carbon powder. Preferably, electrodes that are in contact with the sample during the use of the sensor are made of inert materials, such that the electrode does not undergo a net oxidation or a net reduction during the analysis. More preferably, electrodes that are in contact with the sample during the use of the sensor are made of non-ionizing materials, such as carbon, gold, platinum, and palladium. In some instances, ionizing materials, such as silver, can form redox species during the use of the sensor that can adversely influence the measured current or potential of the system.

Metals may be deposited on a base material by deposition of a metal foil, by chemical vapor deposition, or by deposition of a slurry of the metal on the base. Conductive carbon may be deposited, for example, by pyrolysis of a carbon-containing material or by deposition of a slurry of carbon powder. The slurry may contain more than one type of conductive material. For example, the slurry may contain both palladium and carbon powder. In the case of slurry deposition, the fluid mixture may be applied as an ink to the base material, as described in U.S. Pat. No. 5,798,031.

Figure 2:
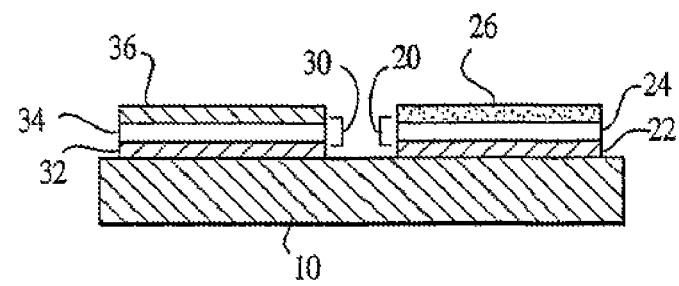
FIG. 2 is an end view diagram of the sensor base of FIG. 1.

The example illustrated in FIG. 2 shows a working electrode 20 and a counter electrode 30, each of which contain a main conductor 22 or 32 and an optional surface conductor 24 or 34. The configuration and the number of components of a given electrode system can be widely varied to optimize the electrical response of the electrodes to the electrochemistry that takes place when a sample is being analyzed. It may be desirable for a main conductor (22 or 32) to be one end of a portion of a single conductive substance, while the connecting conductors (12 or 14) are at the other end of the portion. The optional surface conductor may then function to convert the electrochemical signal into solid-state electron flow to be communicated to a measuring unit via the conductive substance (i.e. flowing from 22 to 12). In one example, main conductors 22 and 32 are pieces of metal foil that are contiguous with the connecting conductors 12 and 14, and the surface conductors 24 and 34 are layers of conductive carbon powder.

Figure 15:
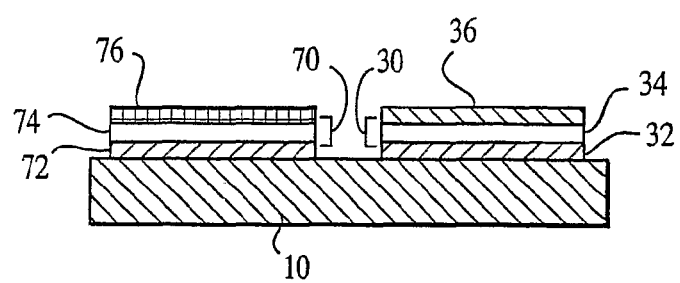
FIG. 15 is a cutaway view diagram of the sensor base of FIG. 13.

The example illustrated in FIG. 15 shows a counter electrode 30 and a third electrode 70, each of which contain a main conductor 32 or 72 and an optional surface conductor 34 or 74. The third electrode components can also be varied to optimize the overall performance of the sensor. It may be desirable for the main conductor 72 to be one end of a portion of a single conductive substance, while the connecting conductor 13 is at the other end of the portion. In one example, main conductor 72 is a piece of metal foil that is contiguous with connecting conductor 13. Optional surface conductor 74 may be, for example, a layer of conductive carbon powder. The third layer 76, containing a soluble redox species, may have a composition that is different from the composition of the second layer 36, or the second and third layers may be identical. In one example, the third layer is a portion of the second layer that is configured to cover the conductors 32 (and optionally 34) and 72 (and optionally 74).

If an electrode contains a surface electrode, it is preferred that the surface electrode is a non-ionizing conductive material. If an electrode is simply a layer of conductive material without a distinct conducting layer on its surface, it is preferred that the conductive material is non-ionizing. More preferably, the surface of the counter electrode, which may or may not be a layer distinct from the main conductor, is a non-ionizing material.

The reagent layers for the working and counter electrodes have compositions that are different from each other. This distinctness allows the reagent layers to be separately optimized to provide a sensor strip having improved electrochemical analysis properties. The layer on the working electrode may contain ingredients that facilitate the reaction of the analyte and the communication of the results of this reaction to the electrode and the connected circuitry. The layer on the counter electrode may contain ingredients that facilitate the free flow of electrons between the sample being analyzed and the electrode and its connected circuitry. To further optimize the system, a third electrode may have a layer containing ingredients that facilitate the free flow of electrons between the sample being analyzed and the electrode and its connected circuitry. Each of the layers may independently contain inert ingredients that are not directly involved in any oxidation-reduction reactions in the electrochemical cell. Examples of such inert ingredients include binding agents such as bentone, polyethylene oxide, or carboxymethyl cellulose; thickening agents such as silica or polyethylene oxide; and one or more buffers.

The layer on the working electrode preferably contains an oxidoreductase enzyme. The oxidoreductase may be specific for a substrate that is the analyte of interest. The oxidoreductase may be specific for a substrate such that the reaction of the oxidoreductase and its substrate is affected by the presence or amount of the analyte of interest. Examples of oxidoreductases and their specific substrates are given in Table I. For example, an alcohol oxidase can be used in the reagent layer to provide a sensor that is sensitive to the presence of alcohol in a sample. Such a system could be useful in measuring blood alcohol concentrations. In another example, glucose dehydrogenase or glucose oxidase can be used in the reagent layer to provide a sensor that is sensitive to the presence of glucose in a sample. This system could be useful in measuring blood glucose concentrations, for example in patients known or suspected to have diabetes. If the concentrations of two different substances are linked through a known relationship, then the measurement of one of the substances through its interaction with the oxidoreductase can provide for the calculation of the concentration of the other substance. For example, an oxidoreductase may provide a sensor that is sensitive to a particular substrate, and the measured concentration of this substrate can then be used to calculate the concentration of the analyte of interest.

TABLE 1

| Oxidoreductase (reagent layer) | Substrate/analyte |
|---|---|
| Glucose dehydrogenase | β-glucose |
| Glucose oxidase | β-glucose |
| Cholesterol esterase; cholesterol oxidase | Cholesterol |
| Lipoprotein lipase; glycerol kinase; glycerol-3-phosphate oxidase | Triglycerides |
| Lactate oxidase; lactate dehydrogenase; diaphorase | Lactate |
| Pyruvate oxidase | Pyruvate |
| Alcohol oxidase | Alcohol |
| Bilirubin oxidase | Bilirubin |
| Uricase | Uric acid |
| Glutathione reductase | NAD(P)H |
| Carbon monoxide oxidoreductase | Carbon monoxide |

The layer on the working electrode may contain one or more mediator substances. The presence of a mediator can enhance the transmission of electrical signal from the enzyme-facilitated redox reaction to the electrode material. Without wishing to be bound by any theory of interpretation, it is believed that mediators may act either as a redox cofactor in the initial enzymatic reaction or as a redox collector to accept electrons from or donate electrons to the enzyme or other species after the reaction has occurred. In the situation of a redox cofactor, the mediator is believed to be the species that balances the redox reaction of the substrate. Thus if the substrate is reduced, the mediator is oxidized. In the situation of a redox collector, another species may have been oxidized or reduced initially to balance the redox reaction of the substrate. This species may be the oxidoreductase itself, or it may be another species such as a redox cofactor.

Mediators in enzymatic electrochemical cells are described, for example in U.S. Pat. No. 5,653,863, which is incorporated herein by reference. In some cases, the mediator may function to regenerate the oxidoreductase. For example, if the enzyme oxidizes a substrate, the enzyme itself is reduced. Interaction of this enzyme with a mediator can result in reduction of the mediator, together with oxidation of the enzyme to its original, unreacted state. Interaction of the mediator with the electrode at an appropriate electrical potential can result in a release of one or more electrons to the electrode together with oxidation of the mediator to its original, unreacted state.

Examples of mediators include OTM and coordination complexes, including ferrocene compounds such as 1,1'-dimethyl ferrocene; and including complexes described in U.S. Pat. No. 5,653,863, such as ferrocyanide and ferricyanide. Examples of mediators also include electroactive organic molecules including coenzymes such as coenzyme pyrroloquinoline quinone (PQQ); the substituted benzoquinones and naphthoquinones disclosed in U.S. Pat. No. 4,746,607, which is incorporated herein by reference; the N-oxides, nitroso compounds, hydroxylamines and oxines specifically disclosed in EP 0 354 441, which is incorporated herein by reference; the flavins, phenazines, phenothiazines, indophenols, substituted 1,4-benzoquinones and indamines disclosed in EP 0 330 517, which is incorporated herein by reference; and the phenazinium and phenoxazinium salts disclosed in U.S. Pat. No. 3,791,988, which is incorporated herein by reference. A review of electrochemical mediators of biological redox systems can be found in *Analytica Clinica Acta*. 140 (1982), pages 1-18. Examples of electroactive organic molecule mediators also include those described in U.S. Pat. No. 5,520,786, which is incorporated herein by reference, including 3-phenylimino-3H-phenothiazine (PIPT), and 3-phenylimino-3H-phenoxazine (PIPO).

The reagent layer on the counter electrode contains a soluble redox species. The soluble redox species undergoes the opposite reaction relative to the reaction of the substrate of the oxidoreductase, and in so doing is converted into its counterpart species of the redox pair. For example, if the analyte is reduced, the soluble redox species is oxidized; and if the analyte is oxidized, the soluble redox species is reduced. The counterpart species of the redox pair may also be present in the layer, but it is preferably present in a concentration lower than the concentration of the primary redox species. More preferably, the redox species in the reagent layer on the counter electrode is exclusively the soluble redox species that undergoes the opposite reaction relative to the reaction of the substrate of the oxidoreductase.

A soluble redox species may be an electroactive organic molecule, it may be an organotransition metal complex, it may be a transition metal coordination complex, or it may be mixtures of any of these. For example, organic molecules such as coenzyme pyrroloquinoline quinone (PQQ), substituted benzoquinones and naphthoquinones, N-oxides, nitroso compounds, hydroxylamines, oxines, flavins, phenazines, phenothiazines, indophenols, indamines, phenazinium salts and phenoxazinium salts may each be a soluble redox species.

A soluble redox species may be an organotransition metal complex or a transition metal coordination complex. Many transition metals occur naturally as compounds with hydrogen, oxygen, sulfur, or other transition metals, and these transition metals are generally observed in one or more oxidation states. For example iron, chromium, and cobalt are typically found in oxidation states of +2 (i.e. II) or +3 (i.e. III). Thus, iron (II) and iron (III) are two species of a redox pair. Many elemental metals or metal ions, however, are only sparingly soluble in aqueous environments, limiting their utility as redox species in balancing the oxidation-reduction reactions in an electrochemical analysis system. Metal ions that are bonded or coordinated to ligands can be made more soluble by their association with those ligands. Typically, the metal in an organotransition metal complex or a transition metal coordination complex is the moiety in the complex that is actually reduced or oxidized. For example, the iron center in ferrocene $[Fe(II)(C_5H_6)_2]$ and in the ferrocyanide ion $[Fe(II)(CN)_6]^{4-}$ is in the +2 formal oxidation state, while the ferricyanide ion $[Fe(III)(CN)_6]^{3-}$ contains iron in its +3 formal oxidation state. Ferrocyanide and ferricyanide together form a redox pair, and either one can function as the soluble redox species in the reagent layer on the counter electrode, depending on the type of oxidoreductase used on the working electrode. An example of a redox pair containing transition metal coordination complexes is the combination of two species of ruthenium hexaamine, $[Ru(III)(NH_3)_6]^{3+}$ and $[Ru(II)(NH_3)_6]^{2+}$.

The species of the redox pair that is present in the reagent layer on the counter electrode, referred to as the first species, is preferably present in a greater molar amount than its counterpart species (i.e. the second species) of the same redox pair. Preferably, the molar ratio of the first species to the second species is at least 1.2:1. More preferably, the molar ratio of the first species to the second species is at least 2:1. Still more preferably, the molar ratio of the first species to the second species is at least 10:1. Still more preferably, the molar ratio of the first species to the second species is at least 100:1. Still more preferably, the second species of the redox pair is present in an amount of 1 part per thousand (ppt) or less prior to the use of the sensor strip in an analysis. Still more preferably, the second species of the redox pair is present in an amount of 1 part per million (ppm) or less prior to the use of the sensor strip in an analysis.

Preferably, the soluble redox species is solubilized in the sample and mixes with the analyte and other sample constituents. The soluble redox species will, over time, mix with the enzyme and the mediator, although this may not occur to any measurable degree over the course of the analysis. The soluble redox species is not separated from the liquid sample by a mechanical barrier, nor is it separate from the liquid sample by virtue of its existence in a separate phase that is distinct from the liquid sample.

In another preferred embodiment, a soluble redox species is chosen having a standard reduction potential of +0.24 volts or greater, versus the standard hydrogen electrode (SHE). In yet another preferred embodiment, a soluble redox species is chosen having a standard reduction potential of +0.35 volts or greater, versus SHE. In yet another preferred embodiment, a redox species having a reduction potential of about +0.48 volts versus SHE (in 0.01 M HCl) is chosen.

Thus, a wide variety of combinations of oxidoreductases, mediators, and soluble redox species can be used to prepare an electrochemical analytical sensor. The use of soluble redox species having higher or lower oxidation numbers relative to their counterpart species in the redox pair is dictated by the type of reaction to be performed at the working electrode. In one example, the analyte undergoes oxidation by interaction with an oxidase or a dehydrogenase. In this case, the more concentrated redox species on the counter electrode has the higher oxidation number. A specific example of this situation is the analysis of glucose using glucose oxidase or glucose dehydrogenase. In another example, the analyte undergoes reduction by interaction with a reductase. In this case, the more concentrated redox species on the counter electrode has the lower oxidation number. In either of these examples, the mediator may be the same substance as the more concentrated redox species on the counter electrode or the redox species of another redox pair.

If a third electrode is present in the sensor, it will also include a reagent layer containing a soluble redox species as described for the counter electrode reagent layer. Preferably the third electrode reagent layer is identical to the counter electrode reagent layer. If the reagent layers on the third and counter electrodes are identical, then it may be desirable simply to coat both electrodes with a single portion of a reagent layer composition.

Figure 4:
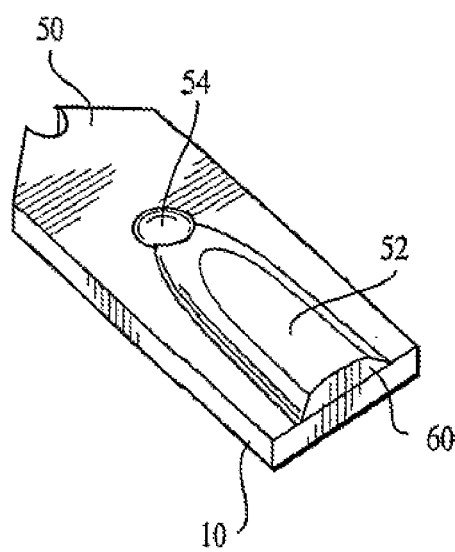
FIG. 4 is a perspective view diagram of a completely assembled sensor strip.

Electrochemical sensors can be used to measure the amount of an analyte that is a substrate for the oxidoreductase on the working electrode or that influences the reaction of the oxidoreductase with its substrate. For sensors that are intended to be operated by the patient, it is desirable for the sample to be a small amount of a biological fluid from the patient. It is preferable for the sample to be analyzed directly, without the need for dilution, addition of reagents or other substances, or filtration or other methods of sample purification. Examples of easily obtained biological fluids include blood, urine, and saliva. Referring to FIG. 4, the sample is applied to the electrodes by depositing a drop of the sample onto the opening provided on the input end 60 of the strip, which is opposite the end of the strip that connects to the measuring unit. The sample migrates to the area between the lid on top and the working electrode and the counter electrode on the bottom. It is helpful for the lid to have an opening 54 to allow the air inside the strip to be vented upon application of the liquid sample. The area between the lid and the base may contain a substance that retains liquid and immobilizes the sample and its contents in the area around the electrodes. Examples of such substances include water-swellable polymers, such as carboxymethyl cellulose and polyethylene glycol; and porous polymer matrices, such as dextran and polyacrylamide.

If a sample contains a substrate for the oxidoreductase, the redox reaction between the substrate and the enzyme can begin once the reagent layer and the sample are in contact. The electrons produced or consumed from this redox reaction can be determined by applying an electrical potential (i.e. voltage) between the working electrode and the counter electrode, and measuring the current. The current can be correlated with the concentration of the substrate in the sample, provided the electrochemical strip system has been calibrated with samples containing known amounts of substrate. The measuring unit preferably contains the necessary circuitry and microprocessors to provide useful information such as the concentration of the substrate in the sample, the concentration of the substrate in the body of the patient, or the relevant concentration of another substance that is related to the measured substrate.

The electrons produced or consumed by the reaction of the oxidoreductase with its substrate are translated into a measurable current when a closed circuit is provided by the counter electrode. The reaction that occurs at the counter electrode is opposite that of the reaction occurring at the working electrode. Thus, the counter electrode supplies or accepts electrons to the sample through the reaction of one or more ingredients of the reagent layer, depending on the type of redox reaction occurring at the working electrode. For example, if oxidation occurs at the working electrode, reduction occurs at the counter electrode.

It may be desirable to delay the measuring of current in the system until a given time after a voltage has been applied. Due to the complicated kinetic nature of the electrochemistry within the sample, the redox reactions may not reach a "steady state" in which the reaction rates have stabilized for a period of between a fraction of a second to several minutes. Measurements before or after this steady state has been achieved can provide erroneous measurements of current, and thus of the concentration of the analyte. Preferably, current measurements begin about 20 seconds after the application of the sample.

Preferably, the voltage initially is applied to the system at the same time as, or immediately after, the deposition of the sample. The initial application of voltage is maintained for 10 seconds and is then stopped, such that there is no applied voltage for a delay time of 10 seconds. After this delay time the voltage is applied again, and the current is monitored, for a read time of 10 seconds.

For sensor strips containing a third electrode, the applied voltage can be monitored by way of the third electrode. Any drift in the intended value of the electrical potential provides feedback to the circuitry through the third electrode, so that the voltage can be adjusted appropriately.

Figure 14:
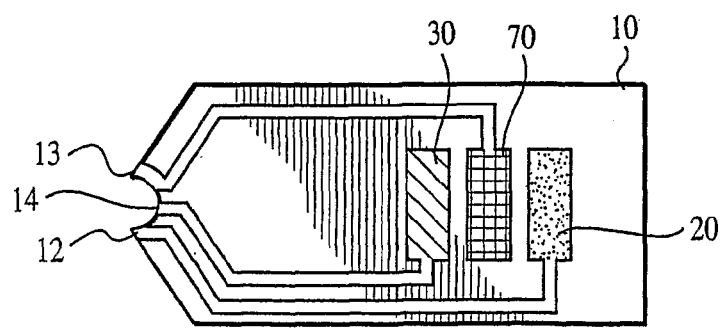

The use of a third electrode may be desirable for some applications. Increased precision in the applied voltage can provide for better accuracy in the measurement of the analyte. When using a third electrode, it may also be possible to reduce the size of the counter electrode or to apply a smaller amount of the redox species to the counter electrode. If the third electrode is positioned upstream of the counter electrode, as illustrated in FIG. 14, then it may be possible to detect when insufficient sample has been applied to the strip, a situation referred to as "underfill." Underfill detection may occur when there is sufficient sample to complete the circuit between the working electrode and the third electrode, but not to cover the counter electrode. The lack of electrical current in the cell can be converted electronically into a signal to the user, instructing the user to add additional sample to the strip.

Electrochemical sensor strips containing separately optimized reagent layers for the working and counter electrodes can provide for improved performance relative to conventional sensor strips. The species of the redox pair on the counter electrode, which undergoes an oxidation-reduction reaction of opposite type with respect to the substrate, should be present in a larger molar ratio than the ratio of 1:1 that is typically used. This larger molar ratio of the redox species does not produce significant interference with the oxidation-reduction reactions occurring near the working electrode during the time necessary for analysis. Also, the high concentration of the redox species provides for a relatively stable electrochemical environment for the counter electrode. Although the redox species is being consumed (i.e. converted into its counterpart species), it maintains a high enough concentration such that a relatively constant linear relationship exists between the measured current and the analyte concentration for the time scale of the analysis.

The large molar ratio of the soluble redox species on the counter electrode can also increase the shelf life of the sensor strip. A small degree of spontaneous conversion of the soluble redox species into its counterpart species can occur during the time between the manufacture of the strip and its use with a sample. Since the relative concentration will remain high, the sensor can still produce accurate results.

EXAMPLES

Example 1

Preparation of Electrode Pairs on a Base

Figure 3:
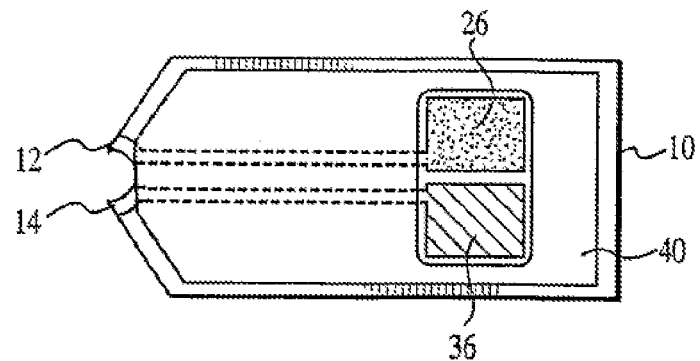
FIG. 3 is a top view diagram of a sensor base and electrodes under a dielectric layer.

Electrodes were formed on a base of insulating material using techniques described in U.S. Pat. Nos. 5,798,031 and 5,120,420. Referring to FIG. 1, silver paste was deposited by screen printing onto a polycarbonate strip 10. This paste was printed in a pattern 12 and 14 to form the electrical contacts and the lower layer of the electrodes. Referring to FIG. 2, an ink containing conductive carbon and a binder was then applied by screen printing in a pattern 24 and 34 to form the top layer of each electrode. Referring to FIG. 3, a dielectric layer containing an acrylate-modified polyurethane was deposited onto the base and the lower layers of the electrodes in a pattern 40 and was then cured by exposure to UV radiation.

Example 2

Sensor Strip Having a Single, Soluble Redox Species on the Counter Electrode

A sensor strip was constructed using a pair of electrodes on a base, prepared as described in Example 1. Referring to FIG. 2, one of the electrodes was made the working electrode by depositing onto the electrode an aqueous mixture 26 of the enzyme glucose dehydrogenase (GDH) in combination with 20 units per microliter of coenzyme PQQ, 24 mM of 3-phenylimino-3H-phenothiazine (PIPT), 8 mM ferrocyanide, and 1% CMC polymer. These ingredients were contained in a 100 mM phosphate buffer having a pH of 7.4. The other electrode was made the counter electrode by depositing onto the electrode an aqueous mixture 36 of 200 mM ferricyanide and 100 mM NaCl in a 100 mM phosphate buffer having a pH of 7.4.

Referring to FIG. 4, after these aqueous mixtures were allowed to dry, the base, dielectric layer and coated electrodes were then bonded to a lid 50 to form the sensor strip. The construction of the lid was performed as described in U.S. Pat. No. 5,798,031. A coating solution of an aqueous polyurethane dispersion was spread on one side of a polycarbonate strip and allowed to dry. The strip was formed into a lid by embossing to form concave area 52 and by punching hole 54. The lid was bonded to the base by aligning and contacting the lid and the base, followed by applying heat to the contact area along the periphery of the structure.

Figure 5:
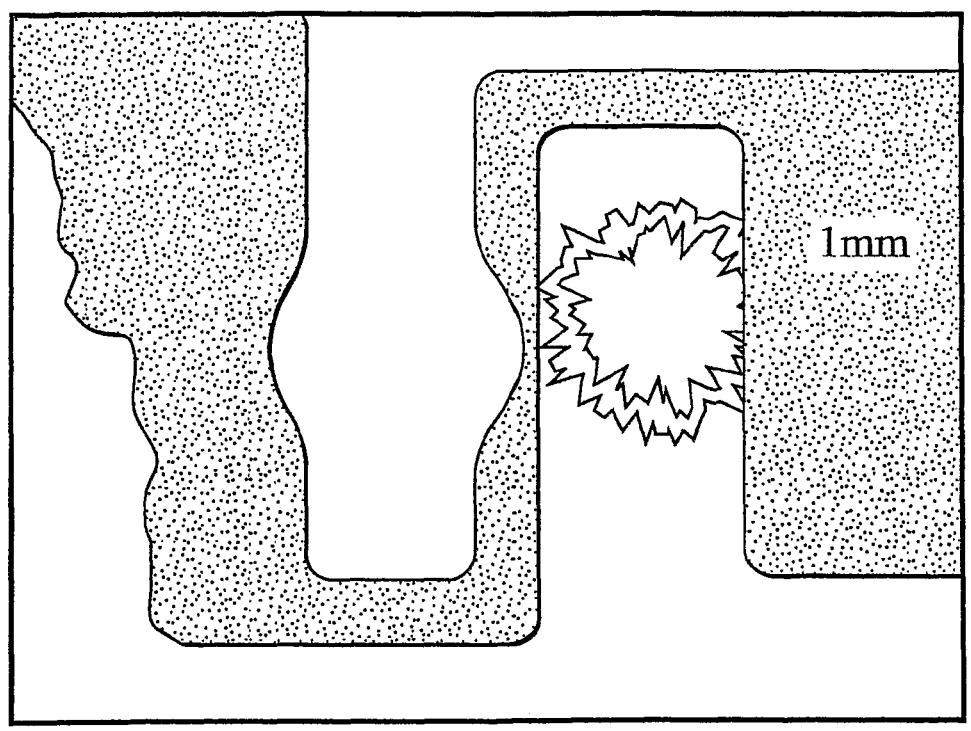
FIG. 5 is a photomicrograph of a working electrode and counter electrode having separate reagent layers.

Referring to FIG. 5, prior to being covered by the lid, the electrode structure was imaged by optical microscopy. The working electrode is the circle on the left, and the counter electrode is the circle on the right.

Example 3

Sensor Strip Having Two Species of a Redox Pair on the Counter Electrode

A sensor strip was constructed as in Example 2, except that the mixture deposited to form the counter electrode contained both ferricyanide (100 mM) and ferrocyanide (100 mM).

Example 4

Cyclic Voltammetric Studies of Sensor Strips

Figure 6:
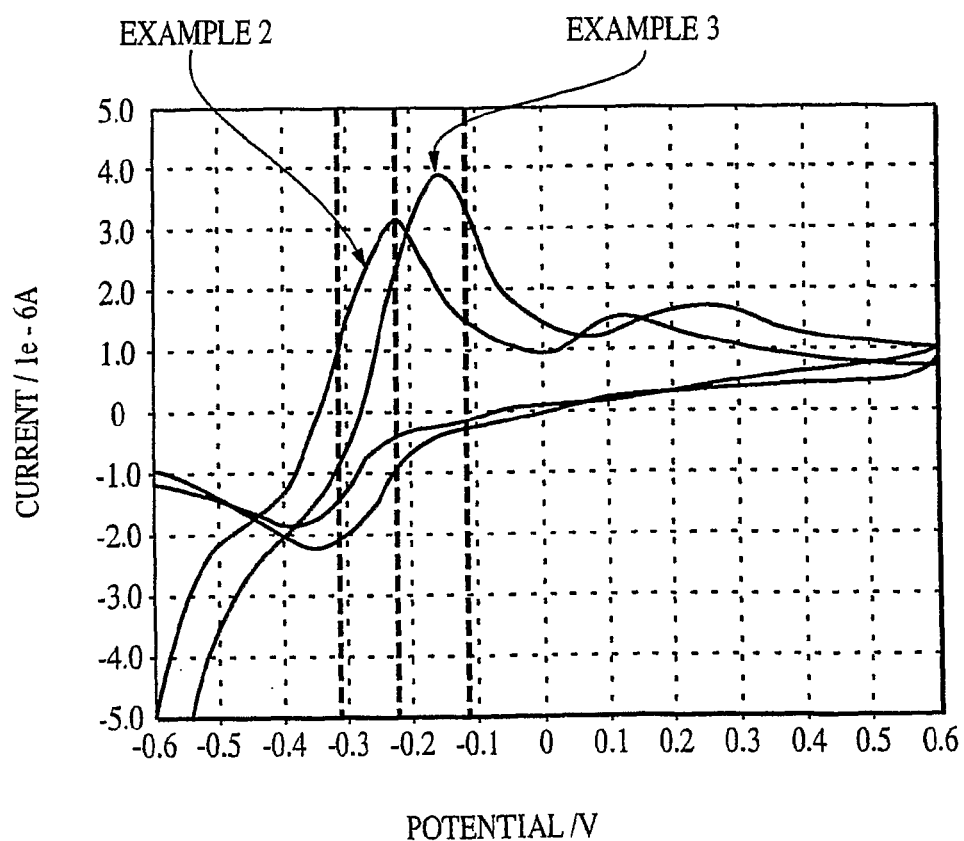
FIG. 6 is a set of cyclic voltammograms for sensor strips having different layers on the counter electrode.

Each of the sensor strips of Examples 2-3 was analyzed by cyclic voltammetry. The strips were re-hydrated with a 100 mM phosphate buffer having a pH of 7.4. Each strip was attached to an analyzer containing a voltage source and a current measuring device. The voltage was set at −0.6V, raised to +0.6V, and lowered again to −0.6V at a rate of 0.025 V/sec, and the current was measured throughout the voltage cycle. A plot of the cyclic voltammograms, measuring the current as a function of applied voltage, for each sensor strip is shown in FIG. 6. Each of the cyclic voltammograms exhibits a peak in the positive current (oxidation peak) due to the oxidation of the PIPT mediator. The oxidation peak occurs near −0.2V for the strip of Example 2 and near −0.15V for the strip of Example 3. These oxidation peaks indicate the potential at which a particular strip should be operated to obtain the maximum current response.

Example 5

Quantification of Glucose Using Sensor Strips

Figure 7:
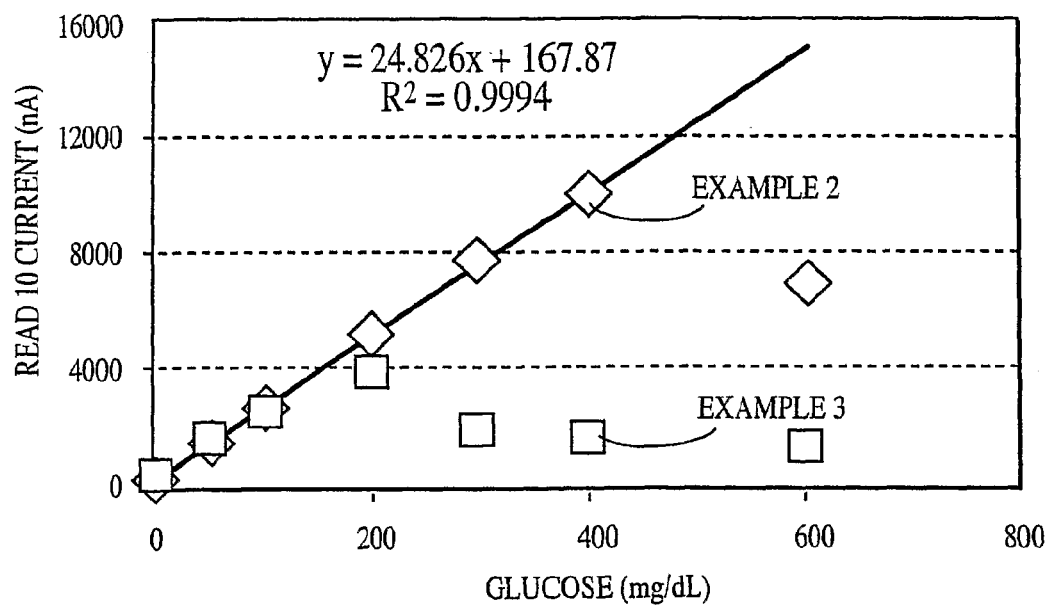
FIG. 7 is a graph of measured current as a function of glucose concentration for sensor strips having different counter electrodes.

The current generated as a function of glucose concentration in a sample was studied for the sensor strips of Examples 2 and 3. Samples containing predetermined amounts of glucose in a 100 mM phosphate buffer having a pH of 7.4 were separately applied to individual sensor strips made according to Example 2 or according to Example 3. A potential of +0.4V was applied to the electrode pair for 10 seconds, followed by 10 seconds of no applied potential. The potential of +0.4V was then applied again for 10 seconds, and the current was measured over during this 10 second interval. FIG. 7 is a plot of the total current over the measurement time period as a function of glucose concentration for Example 2 and Example 3.

The sensors of Example 2 showed a linear increase in average current for glucose concentrations between zero and 400 milligrams per deciliter (mg/dL). The sensors of Example 3 showed a linear increase in average current for glucose concentrations between zero and 200 mg/dL. The range of linear response is thus dependent on the amount of the oxidized species of the redox pair, in this case ferricyanide. The nonlinearity of the current responses is believed to be due to a deficiency in the oxidized species of the redox pair at the counter electrode, so that the oxidation reaction at the working electrode cannot be maintained for higher glucose concentrations.

Sensors of Example 3 exhibit a linear response over a much smaller concentration range than the sensors of Example 2 since the Example 3 sensors contain half as much of the oxidized species of the redox pair.

Example 6

Sensor Strip without Ferrocyanide on the Working Electrode

A sensor strip was constructed as in Example 2, except that the mixture deposited to form the working electrode contained no ferrocyanide.

Example 7

Sensor Strip Having a Reduced Amount of the Soluble Redox Species on the Working Electrode A sensor strip was constructed as in Example 2, except that the mixture deposited to form the working electrode contained 4 mM ferrocyanide.

Example 8

Mediator Contribution

Figure 8:
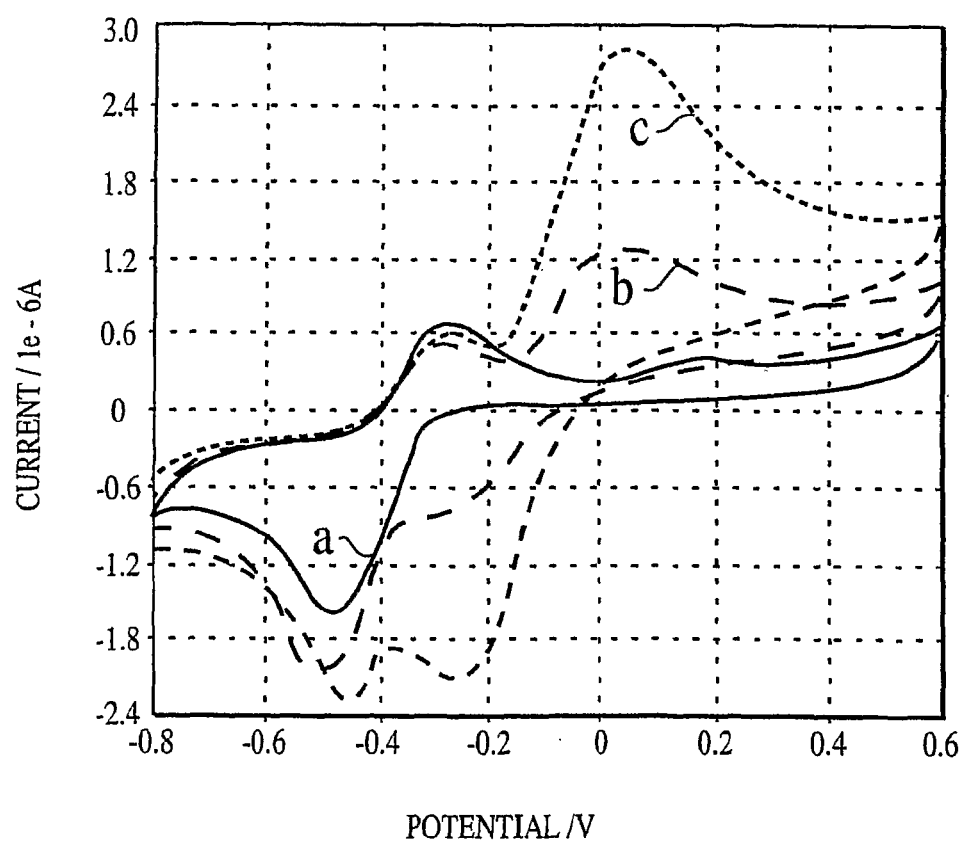
FIG. 8 is a set of cyclic voltammograms for sensor strips having different working electrodes.

Each of the sensor strips of Examples 2, 6 and 7 was analyzed by cyclic voltammetry. The analysis mixtures were 40% hematocrit whole blood containing no glucose. The strips were re-hydrated with 40% whole blood samples. Each strip was attached to an analyzer containing a voltage source and a current measuring device. The voltage was set at −0.8V, raised to +0.6V, and lowered again to −0.8V at a rate of 0.025 V/sec, and the current was measured throughout the voltage cycle. A plot of the cyclic voltammograms, measuring the current as a function of applied voltage, for each sensor strip is shown in FIG. 8.

The voltammogram for the sensor of Example 6 (curve "a") exhibited a clean oxidation peak for PIPT between −0.4V and +0.4V. A local peak in the current around −0.3V was also exhibited in the cyclic voltammograms of the sensors of Examples 2 (curve "c") and 7 (curve "b"); however, the main peaks for these sensors occurred between 0V and +0.1V. All of these potentials are relative to the half cell potential for the reduction of ferricyanide at the counter electrode.

The oxidation peaks at positive potential is due to the oxidation of ferrocyanide at the working electrode. Since the sensor of Example 2 had twice the molar amount of ferrocyanide on the working electrode relative to the sensor of Example 7, the peak current due to the ferrocyanide in the cyclic voltammogram of Example 2 is roughly twice that seen for Example 7. The cyclic voltammogram of the sensor of Example 6 showed no evidence of ferrocyanide oxidation. Since the sensor of Example 6 contained no ferrocyanide on the working electrode, these results indicate that there is no detectable migration of ferrocyanide from the counter electrode to the working electrode during the time scale of this analysis. Ferrocyanide is produced at the counter electrode by the reduction of the ferricyanide which was originally deposited on the counter electrode. In addition, these results demonstrate that an electrochemical biosensor of the present invention can operate with a mediator on the working electrode and a species of a redox pair on the counter electrode, where the mediator is not another species of the redox pair on the counter electrode, Example 9

Examination of Interference of the Counter Electrode Redox Species

Figure 9:
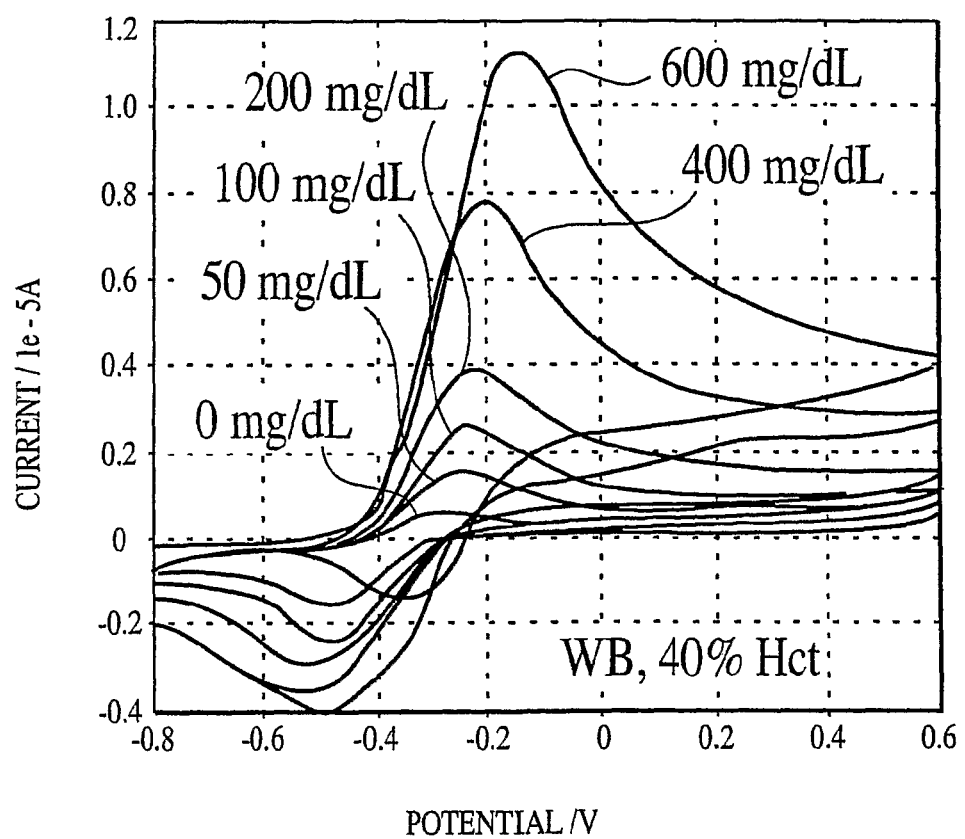
FIG. 9 is a set of cyclic voltammograms at various glucose concentrations for a sensor strip having ferricyanide on the counter electrode, but with no ferrocyanide on the working electrode.

Cyclic voltammograms of the sensor of Example 6 were performed using 40% hematocrit whole blood samples having various glucose concentrations. The voltage was set at −0.8V, raised to +0.6V, and lowered again to −0.8V at a rate of 0.025 V/sec, and the current was measured throughout the voltage cycle. A plot of the cyclic voltammograms, measuring the current as a function of applied voltage, is illustrated in FIG. 9. The measured peak potential for the oxidation peak at about −0.2V became more positive with increased concentrations of glucose. As observed in Example 8 for the cyclic voltammetry performed in the absence of glucose, there is no detectable migration to the working electrode of any ferrocyanide produced at the counter electrode.

Example 10

Quantification of Glucose in Whole Blood

Figure 10:
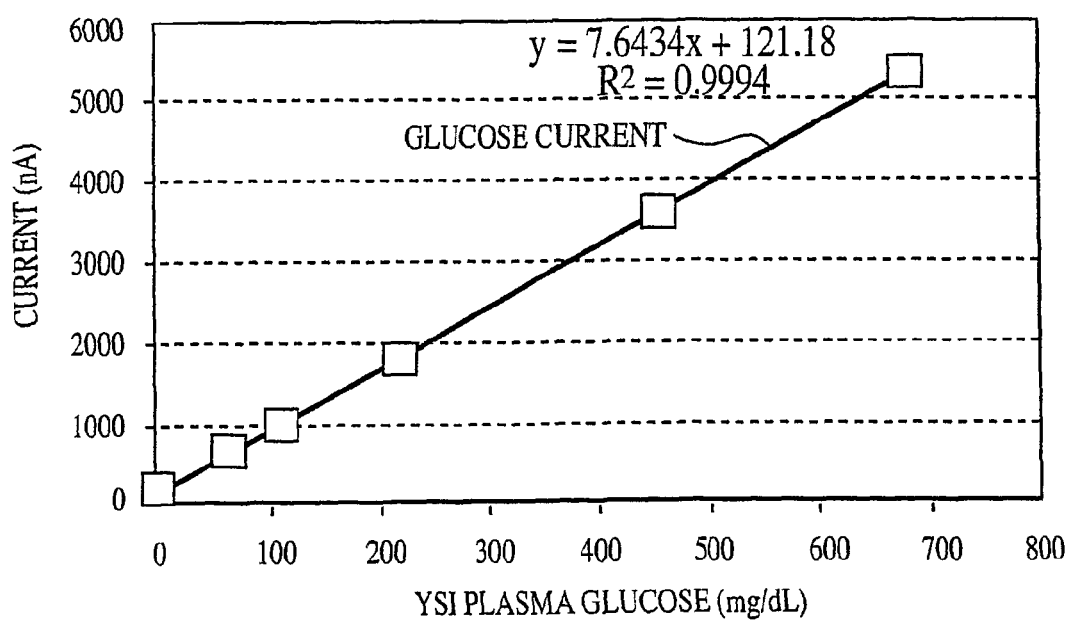
FIG. 10 is a graph of measured current as a function of glucose concentration for a sensor strip.

The current generated as a function of glucose concentration in a sample was studied for the sensor strip of Example 6. Whole blood samples having 40% hematocrit were analyzed for glucose concentration using a YSI glucose analyzer as the reference method. Once the actual glucose concentrations of the various samples were determined, the samples were applied separately to individual sensor strips made according to Example 6. A potential of +0.4V was applied to the electrode pair for 10 seconds, followed by 10 seconds of no applied potential. The potential of +0.4V was then applied again for 10 seconds, and the current was measured over during this 10 second interval. FIG. 10 is a plot of the total current over the measurement time period as a function of glucose concentration for Example 6. The sensors of Examples 6 showed a linear response in current as a function of blood glucose concentration from zero to about 600 mg/dL.

Example 11

Sensor Strip with PIPT on Working and Counter Electrode

Figure 11:
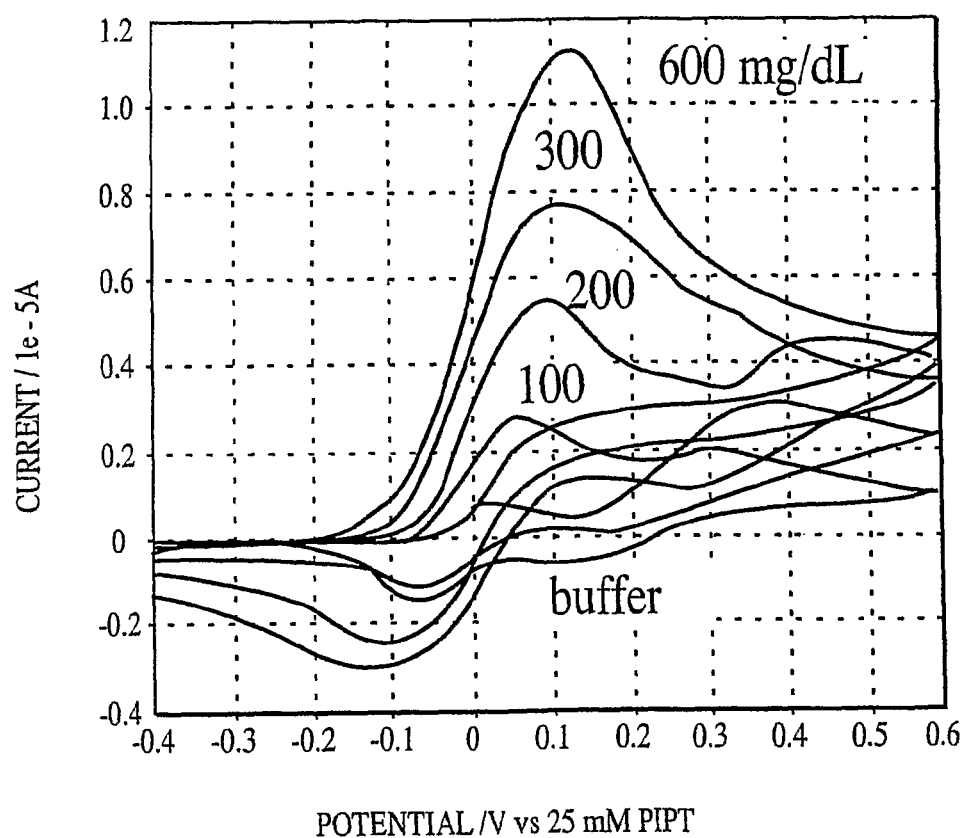
FIG. 11 is a set of cyclic voltammograms at various glucose concentrations for a sensor strip having 3-phenylimino-3H-phenothiazine on both the working and counter electrodes.

A sensor strip was constructed as in Example 1, except that the mixture deposited on the counter electrode contained 25 mM PIPT. Sensor strips made in this way were analyzed by cyclic voltammetry in 100 mM phosphate buffer mixtures at pH 7.4, where the analysis mixtures had various glucose concentrations. The potential was cycled between −0.4V and +0.6V at a rate of 0.025 V/sec. The cyclic voltammograms for these strips are illustrated in FIG. 11.

Since the oxidation of PIPT is measured relative to its own redox potential at the counter electrode, the oxidation/reduction peaks are centered close to 0 volt. On the other hand, the oxidation peak of the ferrocyanide on the working electrode shifted to a higher oxidation potential relative to the PIPT peak. These studies showed the feasibility of using PIPT as the redox species on the counter electrode. The working electrode could contain PIPT, as analyzed in this example, or it could contain ferricyanide as the mediator.

Example 12

Preparation of Sensor Strips Containing Three Electrodes

Figure 12:
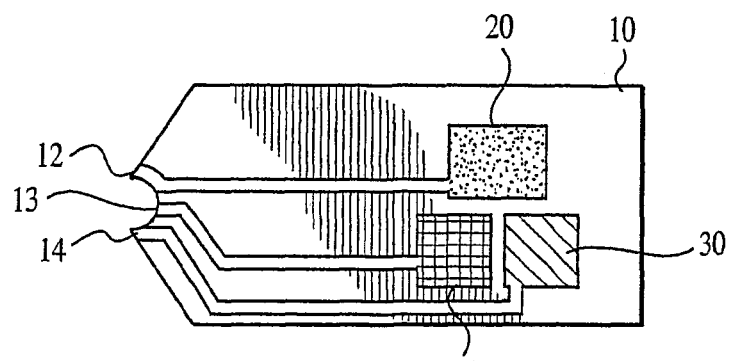
FIGS. 12-14 are top view diagrams of sensor bases containing a working electrode, a counter electrode, and a third electrode.
Figure 13:
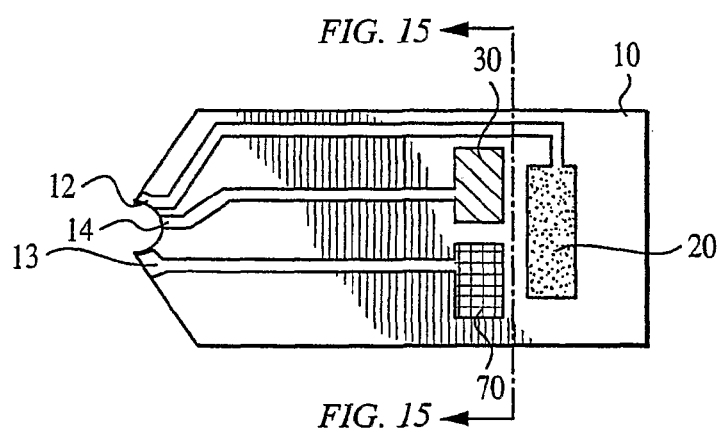

Electrodes are formed on a base of insulating material as described in Example 1, except that a third electrode is also applied to the base. Referring to FIGS. 12-14, silver paste is deposited by screen printing onto a polycarbonate strip 10. This paste is printed in a pattern 12, 13 and 14 to form the electrical contacts and the lower layer of the electrodes. An ink containing conductive carbon and a binder is then applied by screen printing in a pattern 24, 34 and 74 to form the top layer of each electrode. A dielectric layer containing an acrylate-modified polyurethane is deposited onto the base and the lower layers of the electrodes in a pattern to expose the electrodes and is then cured by exposure to UV radiation.

One of the electrodes is made the working electrode by depositing onto the electrode an aqueous mixture 26 of the enzyme glucose dehydrogenase (GDH) in combination with 20 units per microliter of coenzyme PQQ, 24 mM of 3-phenylimino-3H-phenothiazine (PIPT), and 1% CMC polymer. These ingredients are contained in a 100 mM phosphate buffer having a pH of 7.4.

One of the other electrodes is made the counter electrode by depositing onto the electrode an aqueous mixture 36 of 200 mM ferricyanide and 100 mM NaCl in a 100 mM phosphate buffer having a pH of 7.4. The third electrode is made by covering the remaining electrode with a reagent layer 76. The deposition of the reagent layer 76 may be done as a separate step with a third aqueous mixture, or the reagent layer 76 may be applied as a portion of the same aqueous mixture deposited to make the counter electrode.

After these aqueous mixtures are dried, the base, dielectric layer and electrodes are then bonded to a lid to form the sensor strip. A coating solution of an aqueous polyurethane dispersion is spread on one side of a polycarbonate strip and allowed to dry. The strip is formed into a lid by embossing to form a concave area and by punching a hole. The lid is bonded to the base by aligning and contacting the lid and the base, followed by applying heat to the contact area along the periphery of the structure.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

The invention claimed is:

1. A method of quantifying an analyte in a sample, comprising:
   contacting the sample with an electrochemical sensor strip;
      the electrochemical sensor strip before being contacted with the sample comprising a working electrode and a counter electrode, where
         the working and the counter electrodes include compositions that are different from each other,
         the composition of the working electrode includes a mediator and an oxidoreductase enzyme capable of facilitating a redox reaction of the analyte that is specific for the analyte, and
         the composition of the counter electrode includes a first soluble redox species having a standard reduction potential of at least +0.24 volts in relation to a standard hydrogen electrode;
   applying an electrical potential between the working and the counter electrodes;
   stopping the electrical potential between the working and the counter electrodes;
   reapplying the electrical potential between the working and the counter electrodes;
   measuring a current passing through the working and the counter electrodes and the sample, where when the electrical potential is reapplied between the working and the counter electrodes,
      a redox reaction at the working electrode is opposite a redox reaction at the counter electrode,
      the mediator regenerates an oxidation state of the oxidoreductase enzyme after the redox reaction of the analyte,
      the mediator undergoes the same redox reaction as the analyte at the working electrode,
      the mediator undergoes the opposite redox reaction as the analyte when regenerating the oxidation state of the oxidoreductase enzyme,
      the first soluble redox species undergoes the opposite redox reaction of the analyte, and
      there is no detectable migration to the working electrode of reduced first soluble redox species produced at the counter electrode; and
   correlating the current to a concentration of the analyte, where the correlation between the current and the concentration of the analyte is substantially linear from an analyte concentration of about 50 mg/dL to about 400 mg/dL.

2. The method of claim 1, further comprising monitoring the electrical potential between the working and the counter electrodes with a third electrode, the third electrode including a second soluble redox species.

3. The method of claim 2, where the second soluble redox species is the same composition as the first soluble redox species.

4. The method of claim 1, where the mediator is an electroactive organic molecule.

5. The method of claim 4, where the electroactive organic molecule is selected from the group consisting of coenzyme pyrroloquinoline quinone (PQQ), substituted benzoquinones, substituted naphthoquinones, N-oxides, nitroso compounds, hydroxylamines, oxines, flavins, phenazines, phenothiazines, indophenols, indamines, phenazinium salts, phenoxazinium salts, 3-phenylimino-3H-phenothiazines, 3-phenylimino-3H-phenoxazines, and mixtures thereof.

6. The method of claim 4, where the electroactive organic molecule comprises a 3-phenylimino-3H-phenothiazine.

7. The method of claim 4, where the electroactive organic molecule comprises a 3-phenylimino-3H-phenoxazine.

8. The method of claim 1, where the analyte comprises glucose, and the oxidoreductase comprises glucose oxidase or glucose dehydrogenase.

9. The method of claim 1, where the oxidoreductase comprises an enzyme selected from the group consisting of an oxidase and a dehydrogenase; and where the first soluble redox species is a reducible species.

10. The method of claim 2, further comprising measuring a second electrical potential between the third electrode and the working electrode, and adjusting the electrical potential between the working and counter electrodes in response to the second electrical potential.

11. The method of claim 1, where the correlation between the current and the concentration of the analyte is substantially linear from zero to an analyte concentration of about 400 mg/dL.

12. The method of claim 1, where the correlation between the current and the concentration of the analyte is substantially linear from zero to an analyte concentration of about 600 mg/dL.

13. The method of claim 1, where the sensor strip comprises:
   a base;
   a working electrode on the base;
   a counter electrode on the base; and
   a lid mated to the base, such that the lid is over the working and counter electrodes.

14. The method of claim 2, where the sensor strip comprises:
   a base;
   the working electrode on the base;
   the counter electrode on the base;
   the third electrode on the base; and
   a lid mated to the base, such that the lid is over the working, counter, and third electrodes.

* * * * *